(12) United States Patent
Takahashi (10) Patent No.: US 9,192,961 B2
(45) Date of Patent: Nov. 24, 2015

(54) HEAD UNIT, ULTRASONIC PROBE, ELECTRONIC INSTRUMENT, AND DIAGNOSTIC DEVICE

(71) Applicant: SEIKO EPSON CORPORATION, Tokyo (JP)

(72) Inventor: Masaki Takahashi, Chiba (JP)

(73) Assignee: Seiko Epson Corporation, Tokyo (JP)

( * ) Notice: Subject to any disclaimer, the term of this patent is extended or adjusted under 35 U.S.C. 154(b) by 378 days.

(21) Appl. No.: 13/774,223

(22) Filed: Feb. 22, 2013

(65) Prior Publication Data

US 2013/0223193 A1 Aug. 29, 2013

(30) Foreign Application Priority Data

Feb. 24, 2012 (JP) ................................ 2012-038361

(51) Int. Cl.
*B06B 1/06* (2006.01)
*A61B 8/00* (2006.01)

(52) U.S. Cl.
CPC ............. *B06B 1/0622* (2013.01); *A61B 8/4494* (2013.01)

(58) Field of Classification Search
CPC ..... G05D 1/0212; G05D 1/024; G05D 1/021; B25J 13/00; B25J 5/00; Y10S 901/01
USPC ........................................................ 367/140
See application file for complete search history.

(56) References Cited

U.S. PATENT DOCUMENTS

| | | | |
|---|---|---|---|
| 5,318,027 A * | 6/1994 | Fukui | 600/437 |
| 2010/0174194 A1* | 7/2010 | Chiang et al. | 600/447 |
| 2010/0249598 A1* | 9/2010 | Smith et al. | 600/459 |
| 2011/0224487 A1* | 9/2011 | Ogawa | 600/109 |
| 2013/0223184 A1* | 8/2013 | Takahashi | 367/7 |
| 2013/0223193 A1* | 8/2013 | Takahashi | 367/140 |
| 2013/0225993 A1* | 8/2013 | Takahashi | 600/438 |
| 2013/0338507 A1* | 12/2013 | Onishi et al. | 600/459 |
| 2014/0104989 A1* | 4/2014 | Matsuda | 367/138 |
| 2014/0116139 A1* | 5/2014 | Endo | 73/584 |
| 2014/0116140 A1* | 5/2014 | Endo | 73/584 |
| 2014/0116147 A1* | 5/2014 | Endo | 73/658 |
| 2014/0116148 A1* | 5/2014 | Endo | 73/661 |
| 2014/0241112 A1* | 8/2014 | Kano | 367/7 |
| 2015/0027228 A1* | 1/2015 | Endo | 73/641 |
| 2015/0029818 A1* | 1/2015 | Endo | 367/7 |

FOREIGN PATENT DOCUMENTS

| | | | |
|---|---|---|---|
| JP | 2007-142555 A | | 6/2007 |
| JP | 2013172800 A | * | 9/2013 |
| JP | 2013172801 A | * | 9/2013 |

* cited by examiner

*Primary Examiner* — Daniel Pihulic
(74) *Attorney, Agent, or Firm* — Global IP Counselors, LLP (57) ABSTRACT

A head unit for an ultrasonic probe includes a connecting section, an element chip and a supporting member. The connecting section is configured to electrically connect the head unit to a probe main body of the ultrasonic probe. The element chip is configured to be electrically connected to the probe main body through the connecting section. The element chip includes a substrate and an ultrasonic element array. The substrate defines a plurality of openings arranged in an array pattern. The ultrasonic element array includes a plurality of ultrasonic transducer elements, with each of the ultrasonic transducer elements being provided in each of the openings of the substrate. The supporting member supports the element chip.

16 Claims, 10 Drawing Sheets

HEAD UNIT, ULTRASONIC PROBE, ELECTRONIC INSTRUMENT, AND DIAGNOSTIC DEVICE

CROSS-REFERENCE TO RELATED APPLICATIONS

This application claims priority to Japanese Patent Application No. 2012-038361 filed on Feb. 24, 2012. The entire disclosure of Japanese Patent Application No. 2012-038361 is hereby incorporated herein by reference.

BACKGROUND

1. Technical Field

The present invention relates to a head unit, an ultrasonic probe, an electronic instrument, and a diagnostic device.

2. Related Art

An ultrasonic diagnostic device for testing the inside of a human body, for example, has been known as a device in which ultrasonic waves are emitted toward a target and reflected waves are received from the boundary between different acoustic impedances inside the target. In Japanese Laid-Open Patent Publication No. 2007-142555, a technique in which ultrasonic beams are emitted by arranging piezoelectric elements in a matrix array pattern has been disclosed as an ultrasonic probe used for an ultrasonic diagnostic device.

SUMMARY

The technique disclosed in the above mentioned publication, however, has a problem that the entire probe needs to be replaced or repaired when the piezoelectric element is deteriorated over time or damaged, and the repair cost or the like is expensive.

According to some aspects of the present invention, a replaceable head unit, an ultrasonic probe, an electronic instrument, a diagnostic device, and the like are provided.

A head unit for an ultrasonic probe according to one aspect of the present invention includes a connecting section, an element chip and a supporting member. The connecting section is configured to electrically connect the head unit to a probe main body of the ultrasonic probe. The element chip is configured to be electrically connected to the probe main body through the connecting section. The element chip includes a substrate and an ultrasonic element array. The substrate defines a plurality of openings arranged in an array pattern. The ultrasonic element array includes a plurality of ultrasonic transducer elements, with each of the ultrasonic transducer elements being provided in each of the openings of the substrate. The supporting member supports the element chip.

With this aspect, since the probe main body and the head unit can be electrically connected through the connecting section and the head unit can be removably coupled with the probe main body, the head unit can be replaced in a case where the element chip is damaged. As a result, the repair cost can be reduced and user-friendliness can be improved in an ultrasonic diagnostic device, for example.

In the head unit according to the above described aspect of the present invention, the connecting section preferably has a plurality of connecting terminals configured to be connected to the probe main body, and the connecting terminals are preferably disposed on a first surface side of the supporting member and the element chip are supported on a second surface side of the supporting member with the second surface side being a reverse side of the first surface side.

With this configuration, ultrasonic waves can be emitted from the second surface side in which the element chip is supported. Also, since the first surface side on which the plurality of connecting terminals are disposed can be directed toward the probe main body. Consequently, ultrasonic waves can be emitted without being interrupted by the probe main body.

In the head unit according to the above described aspect of the present invention, the connecting section preferably has at least one connector having the connecting terminals, and at least one flexible printed circuit board including a wiring part for connecting the connector and the element chip.

With this configuration, the connector can be disposed on the first surface side of the supporting member. The element chip supported on the second surface side of the supporting member and the connector can be connected through the flexible printed circuit board. Consequently, the element chip and the probe main body can be electrically connected.

In the head unit according to the above described aspect of the present invention, the at least one connector of the connecting section preferably includes a first connector and a second connector, and the at least one flexible printed circuit board of the connecting section includes a first flexible printed circuit board and a second flexible printed circuit board, the first flexible printed circuit board preferably has a first group of wiring sections connecting the first connector to a first group of chip terminals disposed in a peripheral portion along a first side of the element chip, the second flexible printed circuit board preferably has a second group of wiring sections connecting the second connector to a second group of chip terminals disposed in the peripheral portion along a second side opposed to the first side of the element chip, and driving signals for driving the ultrasonic transducer elements are preferably input to the first group of chip terminals and the second group of chip terminals.

With this configuration, the first group of chip terminals and the second group of chip terminals are disposed in the peripheral portion of the element chip along the first side and the second side. In such a case, the first group of chip terminals and the first connector can be connected through the first flexible printed circuit board, and the second group of chip terminals and the second connector can be connected through the second flexible printed circuit board. Further, driving signals are input to the first group of chip terminals and the second group of chip terminals, thereby reducing decrease in the driving signal voltage due to the wiring resistance. Consequently, higher radiation intensity of ultrasonic waves can be obtained.

In the head unit according to the above described aspect of the present invention, the connecting section preferably has a first group of connecting terminals configured to receive signals from or transmit signals to a first group of chip terminals disposed in a peripheral portion along a first side of the element chip, and a second group of connecting terminals configured to receive signals from or transmit signals to a second group of chip terminals disposed in the peripheral portion along a second side opposed to the first side of the element chip. Driving signals for driving the ultrasonic transducer elements are preferably input to the first group of chip terminals and the second group of chip terminals.

With this configuration, when the first group of chip terminals and the second group of chip terminals are disposed in the peripheral portion of the element chip along the first side and the second side, the element chip and the probe main body can be electrically connected through the first group of connecting terminals and the second group of connecting terminals. Further, driving signals are input to the first group of chip terminals and the second group of chip terminals, thereby reducing decrease in the driving signal voltage due to the wiring resistance. Consequently, higher radiation intensity of ultrasonic waves can be obtained.

In the head unit according to the above described aspect of the present invention, the connecting section preferably has a connecting check terminal configured to receive a check signal from or transmit the check signal to the element chip for inspecting the element chip.

With this configuration, since the element chip can be inspected, it is possible to check whether the element chip is abnormal or not, for example, when the head unit is replaced. As a result, a highly reliable ultrasonic probe in which the head unit is replaceable can be achieved.

In the head unit according to the above described aspect of the present invention, the element chip preferably has a check wiring part for inspecting the element chip, and a wiring-breakage-check chip terminal connected to the check wiring part.

With this configuration, it is possible to check whether there is breakage in the wiring of the element chip by the wiring-breakage-check chip terminal. It is thus possible to check whether the element chip is abnormal or not, for example, when the head unit is replaced.

In the head unit according to the above described aspect of the present invention, a wiring-breakage-check signal is preferably input from the probe main body to the wiring-breakage-check chip terminal.

With this configuration, it is possible to check whether there is breakage in the wiring of the element chip by the wiring-breakage-check signal.

In the head unit according to the above described aspect of the present invention, the wiring-breakage-check chip terminal of the element chip preferably includes a first wiring-breakage-check chip terminal disposed on a first side of a signal terminal disposed in the element chip.

With this configuration, it is possible to check whether there is breakage in the wiring of the element chip by using the first wiring-breakage-check chip terminal.

In the head unit according to the above described aspect of the present invention, the wiring-breakage-check chip terminal of the element chip preferably further includes a second wiring-breakage-check chip terminal disposed on a second side of the signal terminal disposed in the element chip, the second side being opposite from the first side. The check wiring part of the element chip preferably includes a breakage check wiring connected to the first wiring-breakage-check chip terminal and the second wiring-breakage-check chip terminal, the breakage check wiring being arranged along a periphery of the ultrasonic element array.

With this configuration, it is possible to check whether there is breakage in the breakage check wiring by the first wiring-breakage-check chip terminal and the second wiring-breakage-check chip terminal.

An ultrasonic probe according to another aspect of the present invention includes a probe main body, and the head unit according the above described aspect with the head unit being removably coupled to the probe main body.

In the ultrasonic probe according to the above described aspect of the present invention, the probe main body preferably has a controlling section configured to perform control for outputting a signal to a chip terminal disposed in the element chip through the connecting section, and the controlling section is preferably configured to perform first control processing when a first head unit is connected to the probe main body as the head unit, and to perform second control processing different from the first control processing when a second head unit is connected to the probe main body as the head unit.

With this configuration, in an ultrasonic diagnostic device, for example, the head unit can be replaced depending on a target to be diagnosed, and control processing suitable for the target to be diagnosed can be conducted. As a result, efficient ultrasonic diagnosis becomes possible.

In the ultrasonic probe according to the above described aspect of the present invention, the controlling section is preferably configured to perform control processing for transmitting and receiving ultrasonic waves corresponding to ultrasonic diagnosis image processing as the first control processing when the first head unit is connected to the probe main body as the head unit, and to perform control processing for transmitting and receiving ultrasonic waves corresponding to blood pressure measurement processing as the second control processing when the second head unit is connected to the probe main body as the head unit.

With this configuration, in the case of conducting ultrasonic diagnosis image processing, the first head unit is connected to the probe main body, and control processing suitable for ultrasonic diagnosis image processing can be conducted. Also, in the case of conducting blood pressure measurement processing, the second head unit is connected to the probe main body, and control processing suitable for blood pressure measurement processing can be conducted.

An electronic instrument according to another aspect of the present invention includes the head unit according to the above described aspects.

A diagnostic device according to another aspect of the present invention includes the head unit according to the above described aspect, and a display section configured to display image data.

BRIEF DESCRIPTION OF THE DRAWINGS

Referring now to the attached drawings which form a part of this original disclosure.

DETAILED DESCRIPTION OF EXEMPLARY EMBODIMENTS

Next, preferred embodiments of the present invention will be explained in detail. The embodiments explained below shall not be construed as unreasonably limiting the subject matter of the present invention described in the claims, and all the elements explained in the embodiments are not necessarily essential to the solving means of the present invention.

1. Ultrasonic Transducer Element

Figure 1A:
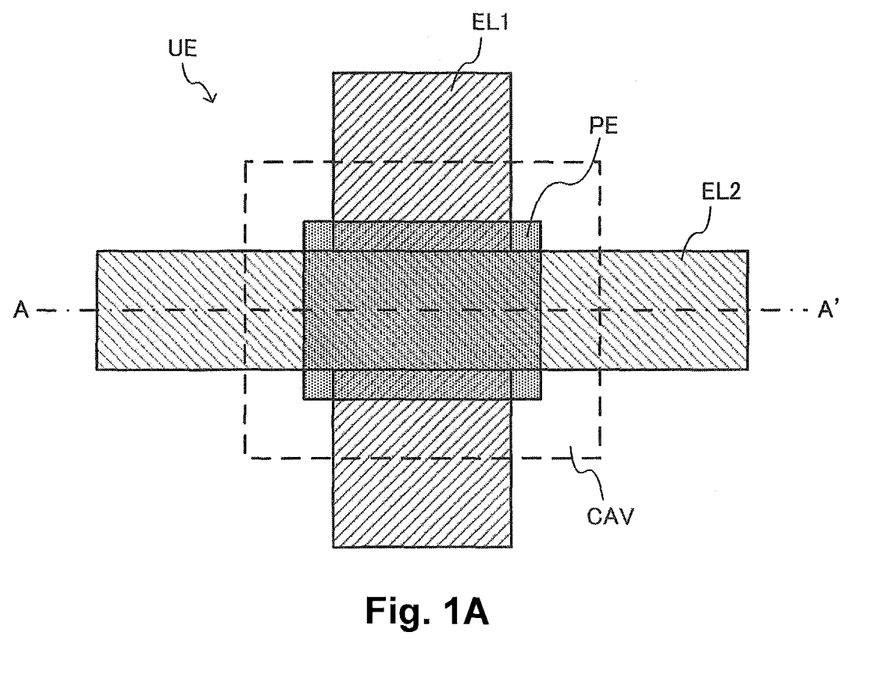
FIG. 1A and FIG. 1B show an example of a basic configuration of an ultrasonic transducer element.
Figure 1B:
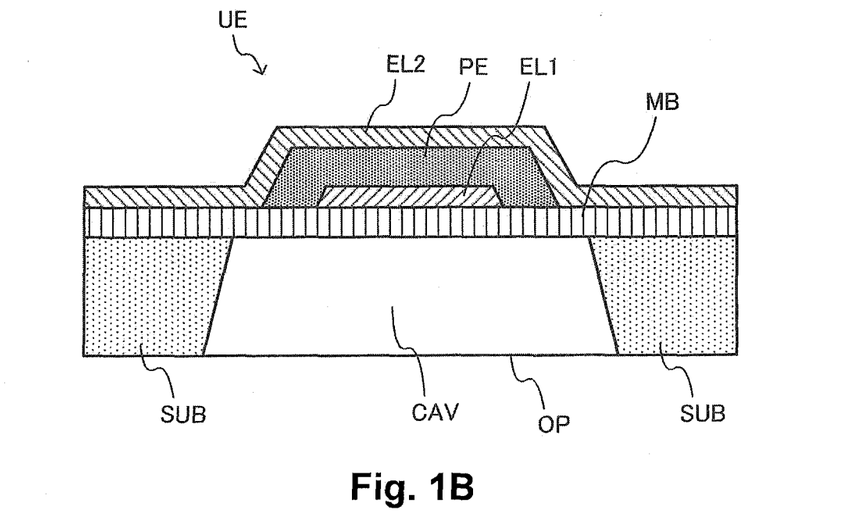

FIG. 1A and FIG. 1B show an example of a basic configuration of an ultrasonic transducer element (one example of an ultrasonic element) UE that is included in a head unit according to the present embodiment. The ultrasonic transducer element UE according to the present embodiment includes a first electrode layer EL1, a piezoelectric body layer PE, a second electrode layer EL2, a membrane (one example of a supporting member) MB, and a cavity region (cavity section) CAV. The ultrasonic transducer element UE according to the present embodiment is not limited to the configuration of FIG. 1, and various changes and modifications are possible. For example, a part of its components can be omitted or replaced with other components, or other components can be added.

FIG. 1A is a plan view of the ultrasonic transducer element UE formed on a substrate (silicon substrate) SUB, seen from a direction perpendicular to the substrate on a side where the element is formed. FIG. 1B is a sectional view along line A-A' of FIG. 1A.

The first electrode layer EU is formed on an upper layer of the membrane MB as a metal thin film, for example. The first electrode layer (lower electrode layer) EU may be a wiring extended outside a region in which the element is formed as shown in FIG. 1A, and connected to the adjacent ultrasonic transducer element UE.

The piezoelectric body layer PE is formed of a PZT (piezoelectric zirconate titanate) thin film, for example. The piezoelectric body layer PE is arranged to cover at least a part of the first electrode layer EL1. The material of the piezoelectric body layer PE is not limited to PZT. Lead titanate ($PbTiO_3$), lead zirconate ($PbZrO_3$), lead lanthanum titanate ($(Pb, La)TiO_3$), or the like may be used.

The second electrode layer (upper electrode layer) EL2 is formed of a metal thin film, for example, and is arranged to cover at least a part of the piezoelectric body layer PE. The second electrode layer EL2 may be a wiring extended outside the region in which the element is formed as shown in FIG. 1A, and connected to the adjacent ultrasonic transducer element UE.

The membrane MB is provided on an upper layer of the cavity region CAV with a two-layer configuration made of an $SiO_2$ thin film and a $ZrO_2$ thin film, for example. The membrane MB supports the piezoelectric body layer PE, the first electrode layer EL1 and the second electrode layer EL2. The membrane MB vibrates in accordance with expansion and contraction of the piezoelectric body layer PE so as to generate ultrasonic waves.

The cavity region CAV is formed from a reverse surface (in which no element is formed) of the silicon substrate SUB by etching such reactive ion etching (RIE). Ultrasonic waves are emitted from an opening OP of the cavity region CAV.

A first electrode of the ultrasonic transducer element UE is formed of the first electrode layer EL1, and a second electrode of the ultrasonic transducer element UE is formed of the second electrode layer EL2. More specifically, a part of the first electrode layer EL1 that is covered by the piezoelectric body layer PE forms the first electrode, and a part of the second electrode layer EL2 that covers the piezoelectric body layer PE forms the second electrode. In other words, the piezoelectric body layer PE is sandwiched by the first electrode and the second electrode.

The piezoelectric body layer PE expands or contracts in an in-plane direction when a voltage is applied between the first electrode and the second electrode, that is, between the first electrode layer EL1 and the second electrode layer EL2. One surface of the piezoelectric body layer PE is attached to the membrane MB through the first electrode layer EL1. Although the second electrode layer EL2 is formed on the other surface of the piezoelectric body layer PE, no other layer is formed on the second electrode layer EL2. Therefore, the piezoelectric body layer PE is difficult to expand or contract on the membrane MB side, and the piezoelectric body layer PE is easy to expand or contract on the second electrode layer EL2 side. Accordingly, when a voltage is applied to the piezoelectric body layer PE, convex warpage occurs on the cavity region CAV side, which causes the membrane MB to warp. When an alternating-current voltage is applied to the piezoelectric body layer PE, the membrane MB vibrates in a film thickness direction, and ultrasonic waves are emitted from the opening OP by the vibration of the membrane MB. The voltage applied to the piezoelectric body layer PE is 10-30 V, for example. The frequency is 1-10 MHz, for example.

2. Element Chip

Figure 2:
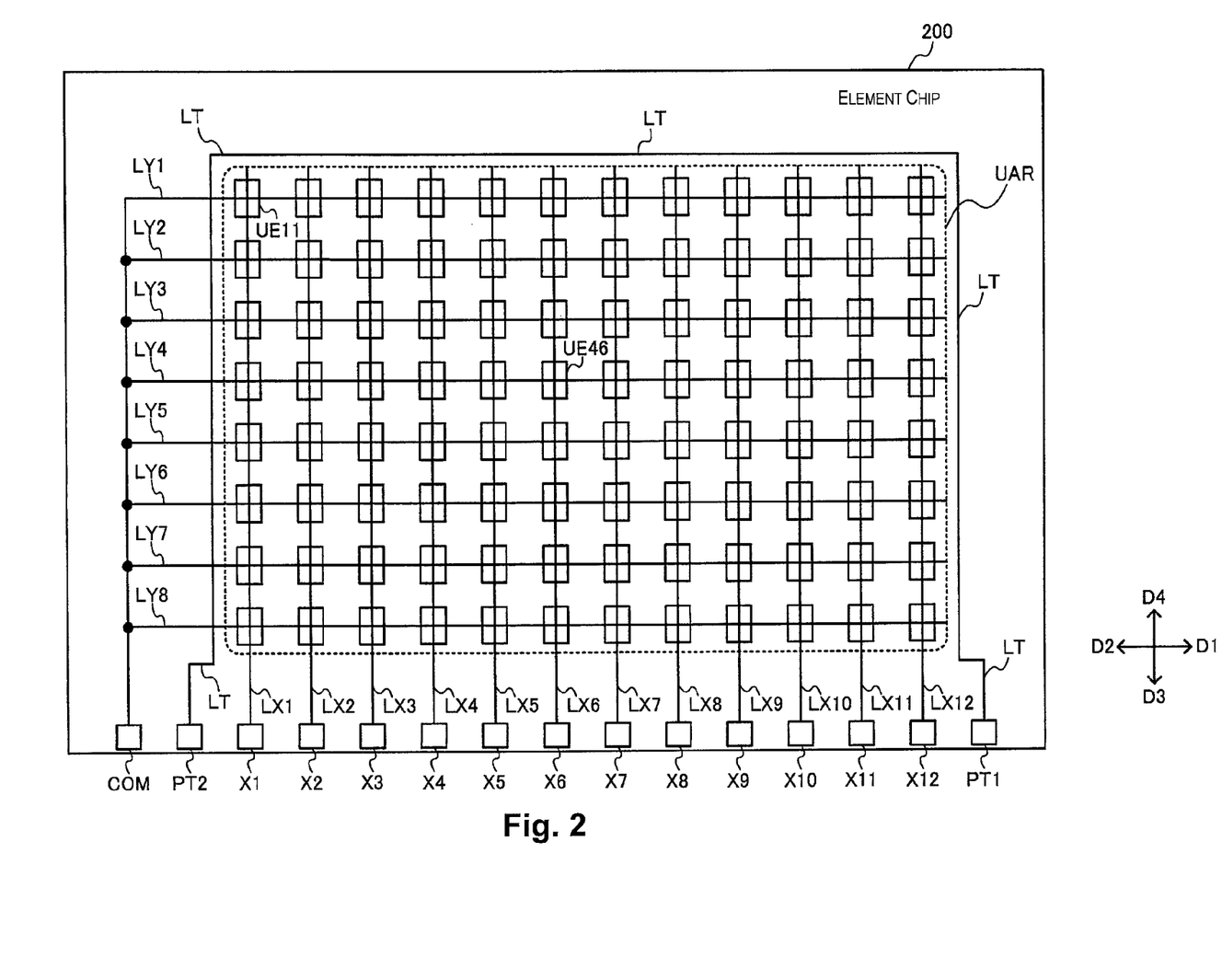
FIG. 2 shows a first example of a configuration of an element chip.

FIG. 2 shows a first example of a configuration of an element chip 200 included in the head unit according to the present embodiment. The element chip 200 of the first example includes an ultrasonic element array UAR. The ultrasonic element array UAR has a substrate in which a plurality of openings are provided in an array pattern, and the plurality of ultrasonic transducer elements UE, each ultrasonic transducer element being provided in each opening of the plurality of openings. The ultrasonic element array UAR further includes first-$n^{th}$ ("n" is an integer of 2 or more) signal lines LX1-LXn, and first-$m^{th}$ ("m" is an integer of 2 or more) common electrode lines LY1-LYm. The element chip 200 further includes first-$n^{th}$ signal terminals X1-Xn, a breakage check wiring (wiring for checking in a broad sense) LT, first and second wiring-breakage-check chip terminals PT1 and PT2, and a common terminal COM. FIG. 2 shows a case where "m" is 8 and "n" is 12 as an example, but other values are possible. The element chip 200 according to the present embodiment is not limited to the configuration of FIG. 2, and various changes and modifications are possible. For example, a part of its components can be omitted or replaced with other components, or other components can be added.

The ultrasonic element array UAR includes the plurality of ultrasonic transducer elements UE provided in a matrix array pattern (array pattern in a broad sense) of "m" rows and "n" columns, for example. The ultrasonic transducer elements UE can be configured as shown in FIG. 1A and FIG. 2. More specifically, as shown in FIG. 2, the ultrasonic transducer elements UE of first-eighth ($m^{th}$ in a broad sense) rows are arranged in a third direction D3, and the ultrasonic transducer elements UE of first-twelfth ($n^{th}$ in a broad sense) columns are arranged in a first direction D1 perpendicular to the third direction D3. In the following explanations, in order to specify a position of the ultrasonic transducer element UE in the array, the ultrasonic transducer element UE positioned in the fourth row and the sixth column is described as UE46, for example.

The arrangement of the ultrasonic transducer element (ultrasonic element) UE is not limited to the matrix pattern of the "m" rows and "n" columns shown in FIG. 2. For example, the so-called zigzag pattern in which an "m" number of ultrasonic transducer elements are arranged in an odd number column and an "m-1" number of ultrasonic transducer elements are arranged in an even number column may be used.

The first-eighth ($m^{th}$ in a broad sense) common electrode lines LY1-LY8 are arranged along the first direction D1 and a second direction D2 in the ultrasonic element array UAR. The $i^{th}$ common electrode line LYi ("i" is an integer satisfying $1 \le i \le 8$) of the first-eighth common electrode lines LY1-LY8 is connected to one of the first electrode and the second electrode of each ultrasonic transducer element UE arranged in the $i^{th}$ row of the ultrasonic element array UAR.

The first-twelfth ($n^{th}$ in a broad sense) signal lines LX1-LX12 are arranged along the third direction D3 or a fourth direction D4 in the ultrasonic element array UAR. The $i^{th}$ signal lines LXj ("j" is an integer satisfying $1 \le j \le 12$) of the first-twelfth signal lines LX1-LX12 is connected to the other of the first electrode and the second electrode of each ultrasonic transducer element UE arranged in the $j^{th}$ column of the ultrasonic element array UAR.

Specifically, for example, regarding the ultrasonic transducer element UE11 shown in FIG. 2, the first electrode is connected to the signal line LX1, and the second electrode is connected to the common electrode line LY1. Also, for example, regarding the ultrasonic transducer element UE46 shown in FIG. 2, the first electrode is connected to the sixth signal line LX6, and the second electrode is connected to the fourth common electrode line LY4.

The first-twelfth signal terminals X1-X12 ($n^{th}$ in a broad sense) are arranged in a peripheral portion along a first side of the element chip 200, for example, and the first-twelfth signal lines LX1-LX12 are connected thereto. During a transmission period of emitting ultrasonic waves, a driving signal for driving the ultrasonic transducer element UE is input to the signal terminals X1-X12. During a reception period of receiving an ultrasonic echo signal, a received signal from the ultrasonic transducer element UE is output from the signal terminals X1-X12.

The common terminal COM is arranged in the peripheral portion along the first side of the element chip 200, for example, and the first-eighth common electrode lines LY1-LY8 are commonly connected thereto.

Here, the first side refers to a side located in the third direction D3 with respect to the center of the element chip 200 in a case where the element chip 200 is a rectangle in a plan view. Also, the peripheral portion along the first side refers to a portion along the first side of the peripheral portion of the element chip 200.

The breakage check wiring (one example of a check wiring) LT is a wiring for checking the element chip 200, and is arranged along the periphery of the ultrasonic element array UAR. One end of LT is connected to the first wiring-breakage-check chip terminal PT1, and the other end is connected to the second wiring-breakage-check chip terminal PT2. A wiring-breakage-check signal from the probe main body is input to the first and second wiring-breakage-check chip terminals PT1 and PT2.

The first wiring-breakage-check chip terminal PT1 is a terminal for checking whether there is breakage in the wiring provided in the element chip 200, and is arranged on the first direction D1 side of the signal terminals X1-X12 provided in the element chip 200, for example.

The second wiring-breakage-check chip terminal PT2 is a terminal for checking whether there is breakage in the wiring provided in the element chip 200, and is arranged on the second direction D2 side of the signal terminals X1-X12 provided in the element chip 200, for example. The second direction D2 is an opposite direction to the first direction D1.

According to the element chip 200 of the present embodiment, it is possible to determine whether the breakage check wiring LT has been broken by checking existence of conduction between the first and second wiring-breakage-check chip terminals PT1 and PT2. With this, in a case where the element chip 200 is damaged, the breakage check wiring LT is broken, and non-conduction occurs between the first and second wiring-breakage-check chip terminals PT1 and PT2. Accordingly, damage and the like of the element chip 200 can be detected.

Figure 3:
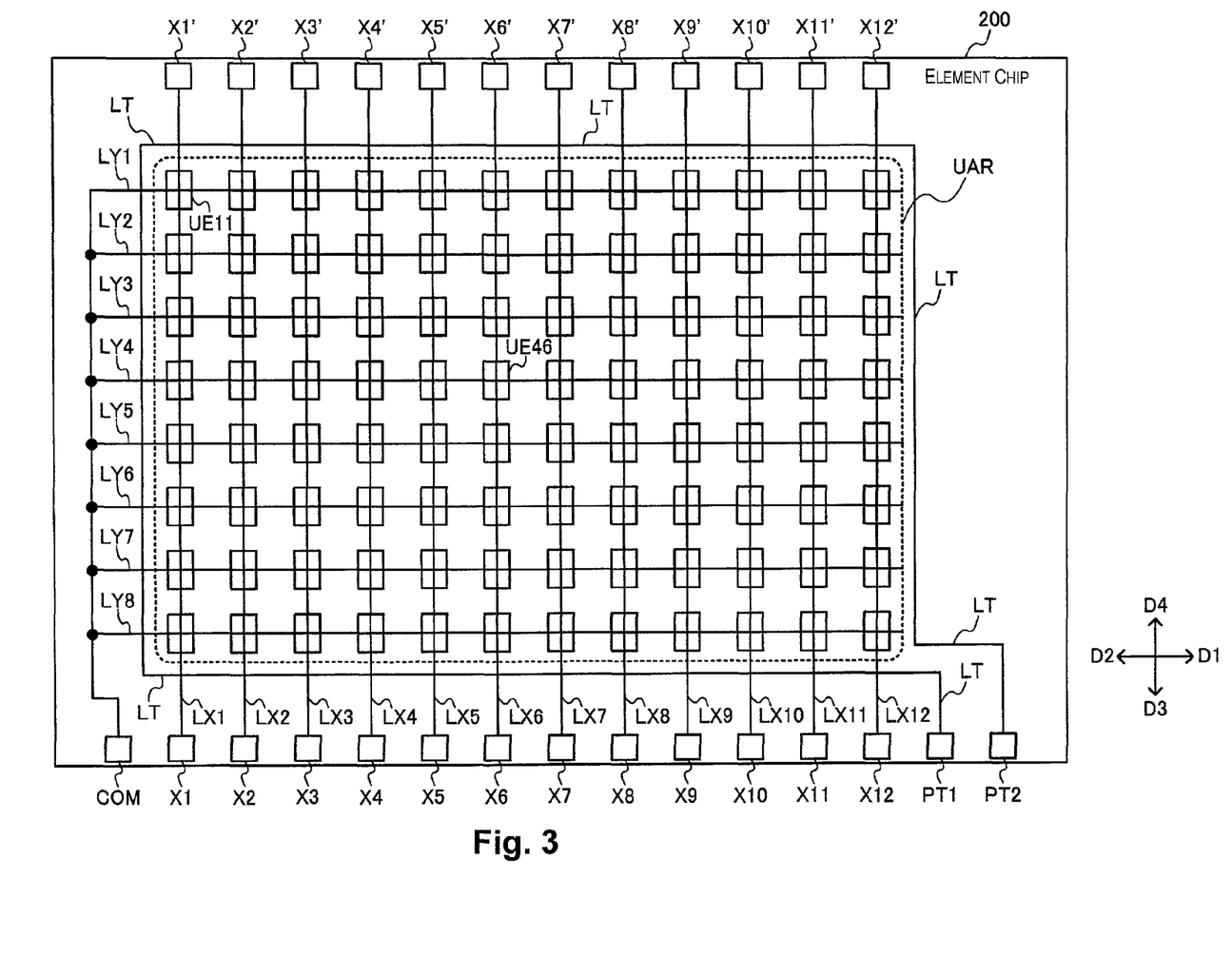
FIG. 3 shows a second example of the configuration of the element chip.

FIG. 3 shows a second example of the configuration of the element chip 200 included in the head unit according to the present embodiment. The element chip 200 of the second example includes the ultrasonic element array UAR, the first-$n^{th}$ ("n" is an integer of 2 or more) signal lines LX1-LXn, the first-$m^{th}$ ("m" is an integer of 2 or more) common electrode lines LY1-LYm, the first-$n^{th}$ signal terminals X1-Xn (one example of a first group of chip terminals) of the peripheral portion along the first side, first-$n^{th}$ signal terminals X1'-Xn' (one example of a second group of chip terminals) of the peripheral portion along a second side, the breakage check wiring (one example of a check wiring) LT, the first and second wiring-breakage-check chip terminals PT1 and PT2, and the common terminal COM. FIG. 3 shows a case where "m" is 8 and "n" is 12 as an example, but other values are possible. The element chip 200 according to the present embodiment is not limited to the configuration of FIG. 3, and various changes and modifications are possible. For example, a part of its components can be omitted or replaced with other components, or other components can be added.

The ultrasonic element array UAR, the first-eighth ($m^{th}$ in a broad sense) common electrode lines LY1-LY8, and the common terminal COM are similar to those of the first example (FIG. 2). Here, therefore, the detailed explanations are omitted.

The first-twelfth ($n^{th}$ in a broad sense) signal lines LX1-LX12 are arranged along the third direction D3 or the fourth direction D4 in the ultrasonic element array UAR. One ends of the signal lines LX1-LX12 are connected to the signal terminals X1-X12 arranged in the peripheral portion along the first side (side on the third direction D3 side) of the element chip 200, and the other ends are connected to the signal terminals X1'-X12' arranged in the peripheral portion along the second side (side on the fourth direction D4 side) of the element chip 200 opposite to the first side.

The first-twelfth ($n^{th}$ in a broad sense) signal terminals X1-X12 are arranged in the peripheral portion along the first side (side on the third direction D3 side) of the element chip 200, and one ends of the signal lines LX1-LX12 are connected thereto. The first-$n^{th}$ signal terminals X1'-Xn' are arranged in the peripheral portion along the second side (side on the fourth direction D4 side) of the element chip 200 opposite to the first side, and the other ends of the signal lines LX1-LX12 are connected thereto.

Here, the first side refers to a side located in the third direction D3 with respect to the center of the element chip 200 in a case where the element chip 200 is a rectangle in a plan view. Also, the peripheral portion along the first side refers to a portion along the first side of the peripheral portion of the element chip 200. Similarly, the second side refers to a side located in the fourth direction D4 with respect to the center of the element chip 200. Also, the peripheral portion along the second side refers to a portion along the second side of the peripheral portion of the element chip 200.

A driving signal for driving the plurality of ultrasonic transducer element UE is input to the signal terminals X1-X12 (one example of a first group of chip terminals)

arranged in the peripheral portion along the first side of the element chip 200 and the signal terminals X1'-X12' (one example of a second group of chip terminals) arranged in the peripheral portion along the second side of the element chip 200. With this, compared to a case where a driving signal is input to only one end of the signal lines LX1-LX12, decrease in the driving signal voltage due to the wiring resistance of the signal lines LX1-LX12 can be reduced, and thus higher radiation intensity (radiated sound pressure) can be obtained.

The first and second wiring-breakage-check chip terminals PT1 and PT2 are arranged on the first direction D1 side of the signal terminals X1-X12 in the peripheral portion along the first side, for example. The breakage check wiring LT is a wiring for checking the element chip 200, and is arranged along the periphery of the ultrasonic element array UAR. One end of LT is connected to the first wiring-breakage-check chip terminal PT1, and the other end is connected to the second wiring-breakage-check chip terminal PT2.

According to the element chip 200 of the second example, since the breakage check wiring LT can be arranged to surround the periphery of the ultrasonic element array UAR, damage and the like of the element chip 200 can be reliably detected by checking existence of conduction between the first and second wiring-breakage-check chip terminals PT1 and PT2.

The element chip 200 of the present embodiment was explained with reference to FIG. 2 and FIG. 3, but the arrangement of the signal terminals, the wiring-breakage-check chip terminals, and the common terminal is not limited to one shown in FIG. 2 and FIG. 3. For example, the wiring-breakage-check chip terminals may be arranged on the second direction D2 side of the signal terminals X1-X12, or may be arranged on the first direction D1 side or on the second direction D2 side of the signal terminals X1'-X12' in the peripheral portion along the second side.

3. Head Unit

Figure 4:
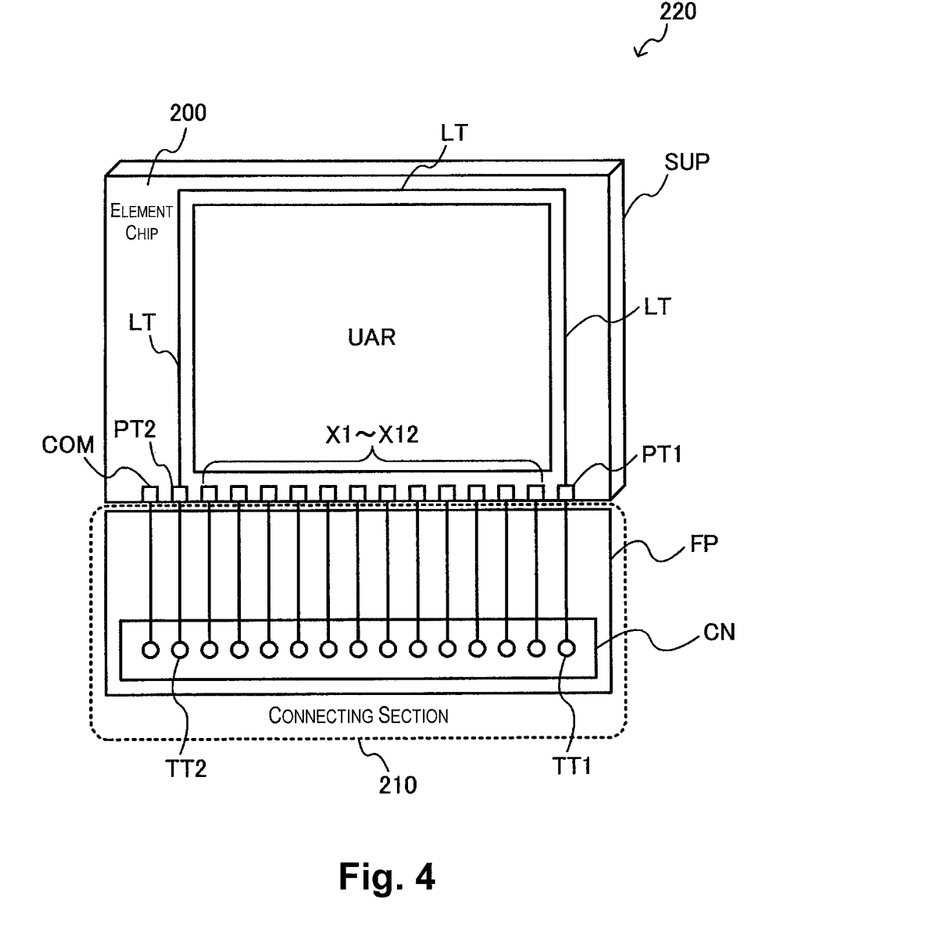
FIG. 4 shows a first example of a configuration of a head unit.

FIG. 4 shows a first example of a configuration of a head unit 220 according to the present embodiment. The head unit 220 of the first example includes the element chip 200, a connecting section 210 and a supporting member SUP. The head unit 220 according to the present embodiment is not limited to the configuration of FIG. 4, and various changes and modifications are possible. For example, a part of its components can be omitted or replaced with other components, or other components can be added.

As for the element chip 200, the element chip of the first example shown in FIG. 2 can be used. As described above, the element chip 200 includes the ultrasonic element array UAR, the signal lines LX1-LX12, the common electrode lines LY1-LY8, the signal terminals X1-X12, the breakage check wiring LT, the wiring-breakage-check chip terminals PT1 and PT2, and the common terminal COM.

The connecting section 210 electrically connects the probe main body of the ultrasonic probe and the head unit 220. The connecting section 210 has a connector CN that has a plurality of connecting terminals connected to the probe main body, and a flexible printed circuit board FP on which a wiring connecting the connector CN and the element chip 200 is formed. The connector CN has connecting check terminals TT1 and TT2 that check the element chip 200. With the connecting section 210, the probe main body and the head unit 220 can be electrically connected, and the head unit 220 can be removable with respect to the probe main body.

The supporting member SUP is a member for supporting the element chip 200. A plurality of connecting terminals are arranged on a first surface side of the supporting member SUP. The element chip 200 is supported on a second surface side of the supporting member SUP. The second surface is a reverse surface of the first surface. The detailed configurations of the element chip 200, the connecting section 210, and the supporting member SUP will be described later.

Figure 5:
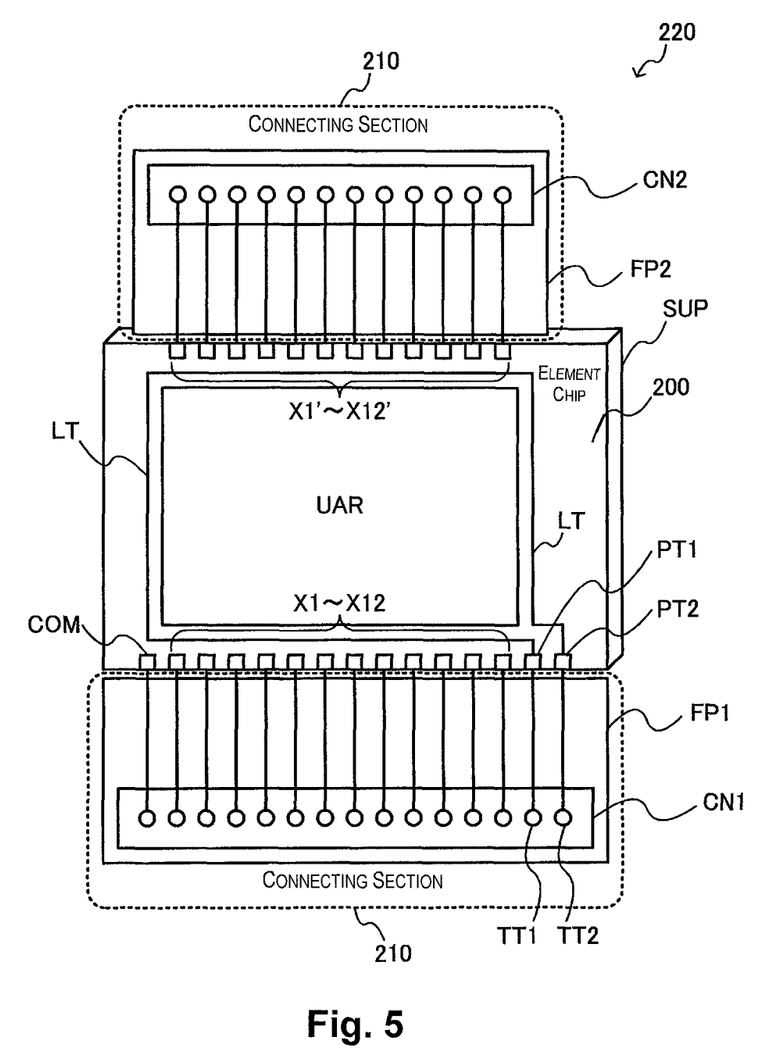
FIG. 5 shows a second example of the configuration of the head unit.

FIG. 5 shows a second example of the configuration of the head unit 220 according to the present embodiment. The head unit 220 of the second example includes the element chip 200, the connecting section 210 and the supporting member SUP. The head unit 220 according to the present embodiment is not limited to the configuration of FIG. 5, and various changes and modifications are possible. For example, a part of its components can be omitted or replaced with other components, or other components can be added.

As for the element chip 200, the element chip of the second example shown in FIG. 3 can be used. As described above, the element chip 200 includes the ultrasonic element array UAR, the signal lines LX1-LX12, the common electrode lines LY1-LY8, the signal terminals X1-X12 (one example of a first group of chip terminals), the signal terminals X1'-X12' (one example of a second group of chip terminals), the breakage check wiring LT, the wiring-breakage-check chip terminals PT1 and PT2, and the common terminal COM.

The connecting section 210 electrically connects the probe main body and the head unit 220. The connecting section 210 has the connector CN that has the plurality of connecting terminals, and the flexible printed circuit board FP on which the wiring connecting the connector CN and the element chip 200 is formed. Specifically, the connecting section 210 has a first connector CN1 and a second connector CN2 as the connector, and also has a first flexible printed circuit board FP1 and a second flexible printed circuit board FP2 as the flexible printed circuit board. The connector CN1 has the connecting check terminals TT1 and TT2 that check the element chip 200.

In the first flexible printed circuit board FP1, there is provided a first group of wirings that connects the first group of chip terminals X1-X12 arranged in the peripheral portion along the first side (side on the third direction D3 side in FIG. 3) of the element chip 200 to the first connector CN1. Also, in the second flexible printed circuit board FP2, there is provided a second group of wirings that connects the second group of chip terminals X1'-X12' arranged in the peripheral portion along the second side (side on the fourth direction D4 side in FIG. 3) of the element chip 200 opposite to the first side to the second connector CN2.

The connecting section 210 is not limited to the configuration of FIG. 5. The connecting section 210 may have a first group of connecting terminals where a signal of the first group of chip terminals X1-X12 arranged in the peripheral portion along the first side of the element chip 200 is input or output, and a second group of connecting terminals where a signal of the second group of chip terminals X1'-X12' arranged in the peripheral portion along the second side of the element chip 200 opposite to the first side is input or output.

With the connecting section 210, the probe main body and the head unit 220 can be electrically connected, and the head unit 220 can be removable with respect to the probe main body.

The supporting member SUP is a member for supporting the element chip 200. A plurality of connecting terminals are arranged on the first surface side of the supporting member SUP. The element chip 200 is supported on the second surface side of the supporting member SUP. The detailed configurations of the element chip 200, the connecting section 210, and the supporting member SUP will be described later.

Figure 6A:
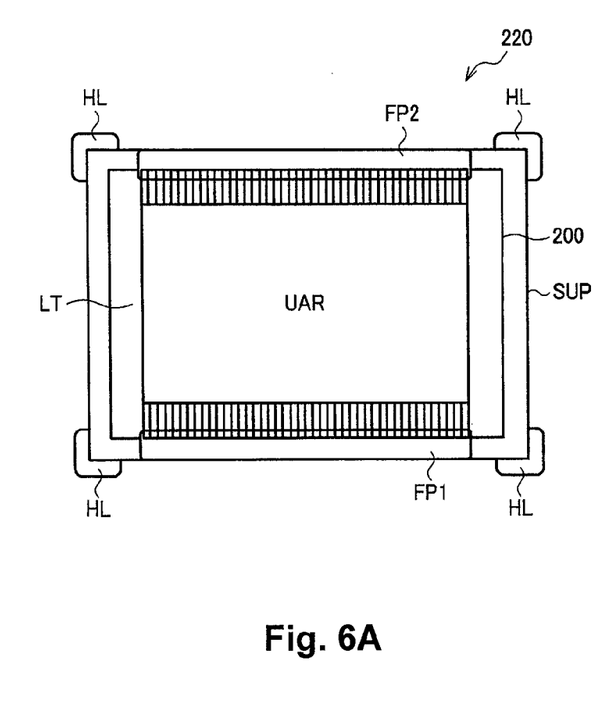
FIG. 6A, FIG. 6B, and FIG. 6C show the details of the second example of the configuration of the head unit.
Figure 6B:
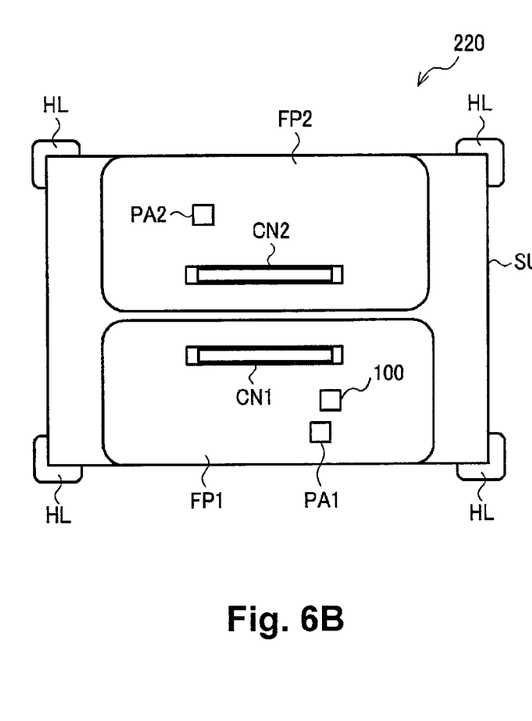
Figure 6C:
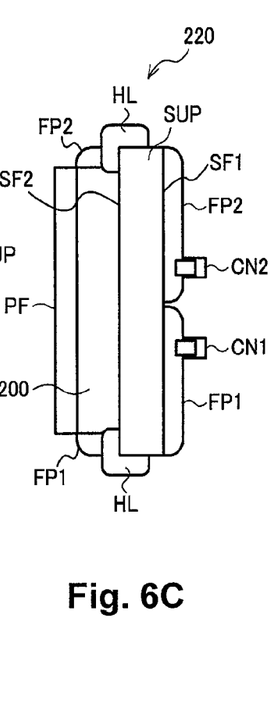

FIG. 6A, FIG. 6B, and FIG. 6C show the details of the second example of the configuration of the head unit 220 according to the present embodiment. FIG. 6A shows the second surface SF2 side of the supporting member SUP, FIG. 6B shows the first surface SF1 side of the supporting member SUP, and FIG. 6C shows a side surface side of the supporting member SUP. The head unit 220 according to the present embodiment is not limited to the configuration of FIG. 6A, FIG. 6B, and FIG. 6C, and various changes and modifications are possible. For example, a part of its components can be omitted or replaced with other components, or other components can be added.

The connector CN1 and the connector CN2 are arranged on the first surface SF1 side of the supporting member SUP, and the other ends of the first flexible printed circuit board FP1 and the second flexible printed circuit board FP2 are connected thereto. Circuits such as preamplifiers PA1 and PA2 may be provided on the first flexible printed circuit board FP1 and the second flexible printed circuit board FP2. The connector CN1 and the connector CN2 are configured to be removable with respect to the corresponding connectors of the probe main body.

The element chip 200 may be provided on the second surface SF2 side of the supporting member SUP. The second surface SF2 is a reverse surface of the first surface SF1. One ends of the first flexible printed circuit board FP1 and the second flexible printed circuit board FP2 are connected to the first group of chip terminals and the second group of chip terminals of the element chip 200. A fixing member HL is provided in each corner portion of the supporting member SUP, and is used for fixing the head unit 220 to a probe case.

The first surface side of the supporting member SUP refers to a normal direction side of the first surface SF1 of the supporting member SUP, and the second surface side of the supporting member SUP refers to a normal direction side of the second surface SF2 that is a reverse surface of the first surface SF1 of the supporting member SUP. The expression that "provided on the first (second) surface side" includes "provided in contact with the first surface SF1 (the second surface SF2)" and "provided through another member".

As shown in FIG. 6C, a protective member (protective film) PF for protecting the element chip 200 is provided in a reverse surface of the element chip 200 (surface in which the opening OP is provided in FIG. 1B).

Figure 7A:
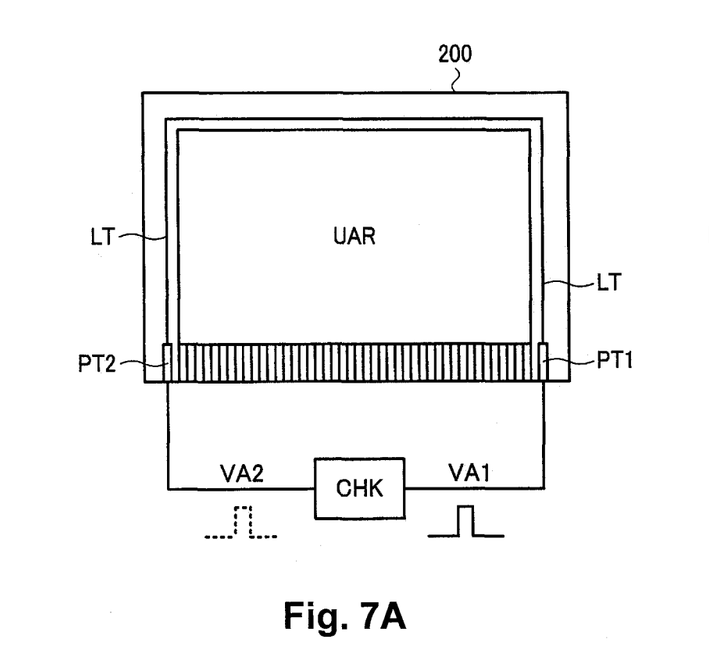
FIG. 7A and FIG. 7B are views explaining wiring-breakage-check process.
Figure 7B:
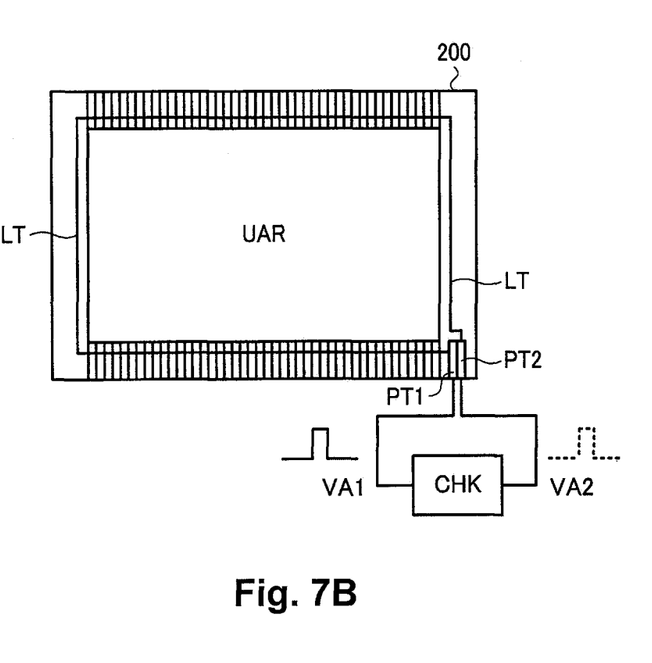

FIG. 7A and FIG. 7B are views explaining wiring-breakage-check by the head unit 220 according to the present embodiment. FIG. 7A shows the case of the element chip 200 of the first example (FIG. 2), and FIG. 7B shows the case of the element chip 200 of the second example (FIG. 3).

As shown in FIG. 7A and FIG. 7B, a wiring-breakage-check signal VA1 is input from a check circuit CHK provided in the probe main body to the wiring-breakage-check chip terminal PT1. When the breakage check wiring LT is not broken, a return signal VA2 of the wiring-breakage-check signal VA1 is input to the check circuit CHK. When the breakage check wiring LT is broken, the return signal VA2 is not input to the check circuit CHK. The check circuit CHK can determine whether the wiring is broken or not by detecting the return signal VA2. The check circuit CHK may output the wiring-breakage-check signal VA1 to PT2, and receive the return signal VA2 from PT1.

Figure 8:
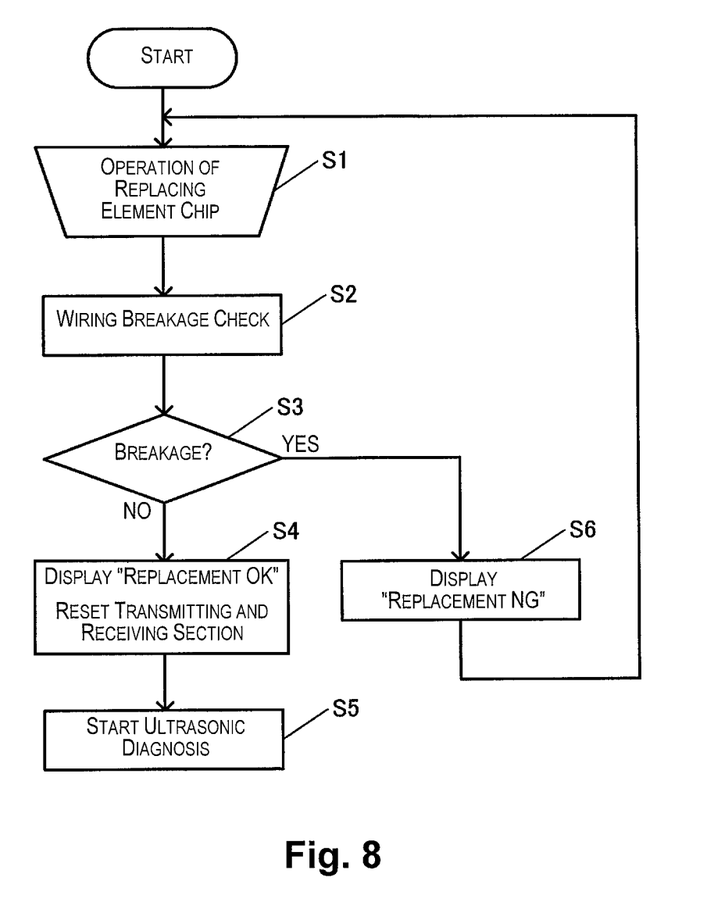
FIG. 8 shows an example of a flow chart of wiring-breakage-check process.

FIG. 8 shows an example of a flow chart of wiring-breakage-check process by the head unit 220 according to the present embodiment.

In a first step S1, an operation of replacing the element chip 200 is conducted. In the next step S2, wiring-breakage-check process is conducted by the check circuit CHK, and it is determined whether there is breakage or not (step S3). When breakage is not detected, it is displayed that the replacement of the element chip 200 is normal ("Replacement OK"), and a transmitting and receiving section is reset (step S4). Next, in step S5, ultrasonic diagnosis is started. The processing of step S4 and step S5 is conducted based on control by a controlling section of a main ultrasonic diagnostic device, for example.

On the other hand, when it is determined that there is breakage in step S3, it is displayed that the replacement of the element chip 200 is not normal ("Replacement NG") (step S6). A user can take actions such as replacement of the element chip with another element chip (step S1).

4. Probe Head and Ultrasonic Probe

Figure 9A:
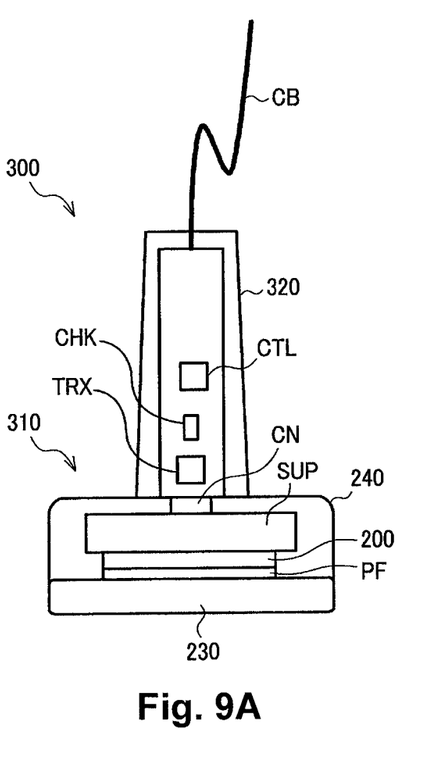
FIG. 9A and FIG. 9B show an example of a configuration of a probe head and an ultrasonic probe.
Figure 9B:
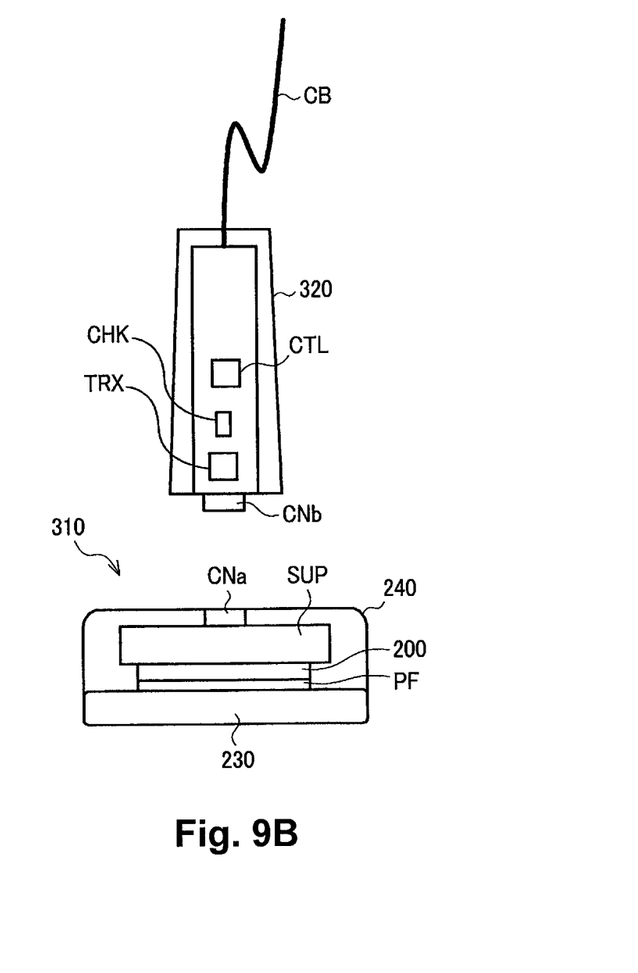

FIG. 9A and FIG. 9B show an example of a configuration of a probe head 310 and an ultrasonic probe 300 according to the present embodiment. FIG. 9A shows a case where the probe head 310 is mounted to a probe main body 320, and FIG. 9B shows a case where the probe head 310 is separated from the probe main body 320.

The probe head 310 includes the head unit 220, a contact member 230 that contacts a material to be tested, and a probe case 240 for storing the head unit 220. The element chip 200 is provided between the contact member 230 and the supporting member SUP.

The probe main body 320 has a transmitting and receiving section TRX, a controlling section CTL, the check circuit CHK, and a probe main body side connector CNb. The transmitting and receiving section TRX conducts processing of transmitting a driving signal for driving the ultrasonic transducer element, and processing of receiving an ultrasonic echo signal (received signal) from the ultrasonic transducer element, based on control of the controlling section CTL. The controlling section CTL conduct processing of controlling the transmitting and receiving section TRX, and the check circuit CHK. The check circuit CHK conducts the above-described wiring-breakage-check process. The probe main body side connector CNb is connected to a head unit (or probe head) side CNa. The probe main body 320 is connected to a main ultrasonic diagnostic device through a cable CB, for example.

Although the head unit 220 is stored in the probe case 240, the head unit 220 can be removed from the probe case 240. With this, only the head unit 220 can be replaced. It is also possible to replace in a state of being stored in the probe case 240, that is, as the probe head 310.

The controlling section CTL conducts control that outputs a signal to the chip terminal provided in the element chip 200 through the connecting section 210. The controlling section CTL can conduct first control processing in a case where the first head unit 220 is connected to the probe main body 320, and conduct second control processing different from the first control processing in a case where the second head unit 220 is connected to the probe main body 320. More specifically, the controlling section CTL conducts control processing for transmitting and receiving ultrasonic waves corresponding to ultrasonic diagnosis image processing to the transmitting and receiving section TRX as the first control processing in a case where the first head unit 220 is connected to the probe main body 320, and conducts control processing for transmitting and receiving ultrasonic waves corresponding to blood pressure measurement processing to the transmitting and receiving section TRX as the second control processing in a case where the second head unit 220 is connected to the probe main body 320.

As described above, according to the head unit, the probe head, and the ultrasonic probe of the present embodiment, only the head unit (or probe head) can be replaced. Consequently, since it is sufficient to replace only the head unit (or probe head) when the element chip is damaged, the repair cost can be reduced and user-friendliness can be improved. Further, it can be expected that hygiene will be improved by making the head unit disposable.

Also, according to the head unit, the probe head, and the ultrasonic probe of the present embodiment, damage of the element chip or bad connection caused at the time of replacement can be detected by providing the breakage check wiring LT in the element chip. As a result, a highly reliable ultrasonic probe can be achieved.

Further, the head unit can be replaced depending on a target to be diagnosed, and control processing suitable for the target to be diagnosed can be conducted. Consequently, efficient ultrasonic diagnosis becomes possible.

Figure 10:
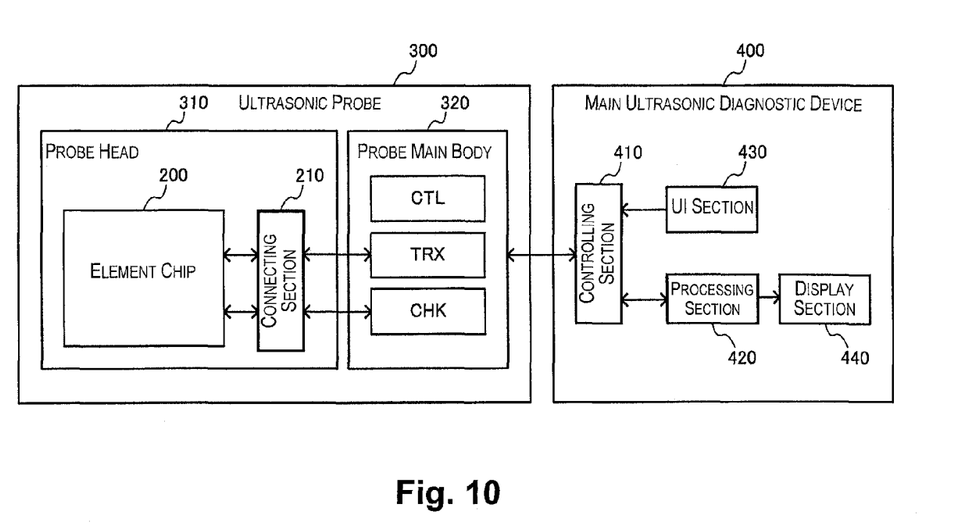
FIG. 10 shows an example of a basic configuration of an ultrasonic diagnostic device.

FIG. 10 shows an example of a basic configuration of a diagnostic device (one example of an electronic instrument) that includes the head unit 220 of the present embodiment. The diagnostic device includes the ultrasonic probe 300 and a main ultrasonic diagnostic device 400. The main ultrasonic diagnostic device 400 includes a controlling section 410, a processing section 420, a UI (user interface) section 430, and a display section 440.

The controlling section 410 conducts processing for receiving and transmitting ultrasonic waves to the transmitting and receiving section TRX together with the controlling section CTL of the probe main body 320. Further, the controlling section 410 conducts control such as image processing of detected data to the processing section 420. The processing section 420 receives detected data from the transmitting and receiving section TRX, and conducts necessary processing such as image processing or generation of image data for display. The UI (user interface) section 430 outputs a necessary order (command) to the controlling section 410 based on an operation conducted by a user (for example, an operation to a touch panel). The display section 440 is a liquid crystal display and the like that displays image data for display from the processing section 420.

Part of processing conducted by the controlling section CTL of the probe main body 320 may be conducted by the controlling section 410 of the main ultrasonic diagnostic device 400. Part of processing conducted by the controlling section 410 of the main ultrasonic diagnostic device 400 may be conducted by the controlling section CTL of the probe main body 320.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the head unit, the ultrasonic probe, the electronic instrument, and the diagnostic device are not limited to the present embodiment, and various changes and modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A head unit for an ultrasonic probe comprising:
   an element chip including
      a substrate defining a plurality of openings arranged in an array pattern, and
      an ultrasonic element array including a plurality of ultrasonic transducer elements, with each of the ultrasonic transducer elements being provided in each of the openings of the substrate; and
   a supporting member including a first surface and a second surface opposing to the first surface, the supporting member supporting the element chip on the second surface; and
   a connecting section including a plurality of connecting terminals and arranged on the first surface of the supporting member, the connecting section electrically connecting to the element chip,
   a thickness direction of the substrate of the element chip being normal to the first surface and the second surface of the supporting member.

2. The head unit according to claim 1, wherein
   the connecting terminals are configured to be connected to a probe main body.

3. The head unit according to claim 1, wherein
   the connecting section has
      at least one connector having the connecting terminals, and
      at least one flexible printed circuit board including a wiring part for connecting the connector and the element chip.

4. The head unit according to claim 3, wherein
   the at least one connector of the connecting section includes a first connector and a second connector, and
   the at least one flexible printed circuit board of the connecting section includes a first flexible printed circuit board and a second flexible printed circuit board,
   the first flexible printed circuit board has a first group of wiring sections connecting the first connector to a first group of chip terminals disposed in a peripheral portion along a first side of the element chip,
   the second flexible printed circuit board has a second group of wiring sections connecting the second connector to a second group of chip terminals disposed in the peripheral portion along a second side opposed to the first side of the element chip, and driving signals for driving the ultrasonic transducer elements are input to the first group of chip terminals and the second group of chip terminals.

5. The head unit according to claim 1, wherein the connecting section has a first group of connecting terminals configured to receive signals from or transmit signals to a first group of chip terminals disposed in a peripheral portion along a first side of the element chip, and a second group of connecting terminals configured to receive signals from or transmit signals to a second group of chip terminals disposed in the peripheral portion along a second side opposed to the first side of the element chip, and driving signals for driving the ultrasonic transducer elements are input to the first group of chip terminals and the second group of chip terminals.

6. The head unit according to claim 1, wherein the connecting section has a connecting check terminal configured to receive a check signal from or transmit the check signal to the element chip for inspecting the element chip.

7. The head unit according to claim 6, wherein the element chip has a check wiring part for inspecting the element chip, and a wiring-breakage-check chip terminal connected to the check wiring part.

8. The head unit according to claim 7, wherein a wiring-breakage-check signal is input to the wiring-breakage-check chip terminal from a probe main body that the connecting terminals are configured to be connected to.

9. The head unit according to claim 8, wherein the wiring-breakage-check chip terminal of the element chip includes a first wiring-breakage-check chip terminal disposed on a first side of a signal terminal disposed in the element chip.

10. The head unit according to claim 9, wherein the wiring-breakage-check chip terminal of the element chip further includes a second wiring-breakage-check chip terminal disposed on a second side of the signal terminal disposed in the element chip, the second side being opposite from the first side, and the check wiring part of the element chip includes a breakage check wiring connected to the first wiring-breakage-check chip terminal and the second wiring-breakage-check chip terminal, the breakage check wiring being arranged along a periphery of the ultrasonic element array.

11. An ultrasonic probe comprising:

a probe main body; and the head unit according to claim 1, the head unit being removably coupled to the probe main body.

12. The ultrasonic probe according to claim 11, wherein the probe main body has a controlling section configured to perform control for outputting a signal to a chip terminal disposed in the element chip through the connecting section, and the controlling section is configured to perform first control processing when a first head unit is connected to the probe main body as the head unit, and to perform second control processing different from the first control processing when a second head unit is connected to the probe main body as the head unit.

13. The ultrasonic probe according to claim 12, wherein the controlling section is configured to perform control processing for transmitting and receiving ultrasonic waves corresponding to ultrasonic diagnosis image processing as the first control processing when the first head unit is connected to the probe main body as the head unit, and to perform control processing for transmitting and receiving ultrasonic waves corresponding to blood pressure measurement processing as the second control processing when the second head unit is connected to the probe main body as the head unit.

14. An electronic instrument comprising the head unit according to claim 1.

15. A diagnostic device comprising:

the head unit according to claim 1; and a display section configured to display image data.

16. The head unit according to claim 1, wherein the supporting member has a plate shape, and the first surface and the second surface are opposed to each other in the thickness direction, which is equal to the direction in which the supporting member is arranged between the element chip and the connecting section.

\* \* \* \* \*